US010098850B2

(12) United States Patent
Wray et al.

(10) Patent No.: US 10,098,850 B2
(45) Date of Patent: Oct. 16, 2018

(54) FORMULATION AND METHOD OF USE OF A TREATMENT FOR SHINGLES PAIN

(71) Applicants: Howard L. Wray, Haines City, FL (US); Aman Singh, Saint Cloud, FL (US)

(72) Inventors: Howard L. Wray, Haines City, FL (US); Aman Singh, Saint Cloud, FL (US)

( * ) Notice: Subject to any disclaimer, the term of this patent is extended or adjusted under 35 U.S.C. 154(b) by 961 days.

(21) Appl. No.: 14/333,121

(22) Filed: Jul. 16, 2014

(65) Prior Publication Data

US 2015/0025152 A1 Jan. 22, 2015

Related U.S. Application Data

(60) Provisional application No. 61/846,690, filed on Jul. 16, 2013.

(51) Int. Cl.

| | |
|---|---|
| *A61K 36/53* | (2006.01) |
| *A61K 36/54* | (2006.01) |
| *A61K 36/752* | (2006.01) |
| *A61K 31/05* | (2006.01) |
| *A61K 31/167* | (2006.01) |
| *A61K 31/125* | (2006.01) |
| *A61K 9/00* | (2006.01) |
| *A61K 31/045* | (2006.01) |

(52) U.S. Cl.
CPC ............ *A61K 31/05* (2013.01); *A61K 9/0014* (2013.01); *A61K 31/045* (2013.01); *A61K 31/125* (2013.01); *A61K 31/167* (2013.01)

(58) Field of Classification Search
CPC ....... A61K 36/53; A61K 36/54; A61K 36/752
USPC ........................................ 424/747, 739, 736
See application file for complete search history.

(56) References Cited

U.S. PATENT DOCUMENTS 4,661,354 A * 4/1987 Finnerty ................ A61K 33/30 424/642
5,961,997 A * 10/1999 Swinehart ................ A61K 8/34 424/401
6,656,928 B1 * 12/2003 McCadden ............ A61K 31/56 514/167

* cited by examiner

*Primary Examiner* — Christopher Robin Tate
*Assistant Examiner* — Deborah A Davis
(74) *Attorney, Agent, or Firm* — Vincent Re PLLC

(57) ABSTRACT

A pharmaceutical formulation for treatment of shingles is provided. The formulation includes between 0.2 mg of menthol per 120 mL of the formulation and 1.0 mg of menthol per 120 mL of the formulation, camphor water, lime water, and a local anesthetic. The local anesthetic includes one of between 0.6 mL of phenol per 120 mL of the formulation and 2.0 mL of phenol per 120 mL of the formulation and between 0.25% concentration by weight of lidocaine and 5% concentration by weight of lidocaine.

15 Claims, 3 Drawing Sheets

| **Table 1** | |
|---|---|
| Menthol | 0.2 mg - 1.0mg |
| Phenol | 0.6 mL - 2.0 mL |
| Camphor water | 60 mL |
| Lime water | Quantity sufficient to make 120 mL of formulation |

FIG. 1

| **Table 2** | |
|---|---|
| Menthol | 0.2 mg - 1.0mg |
| Lidocaine | 0.25% - 5% |
| Camphor water | 60 mL |
| Lime water | Quantity sufficient to make 120 mL of formulation |

FIG. 2

| **Table 3** | |
|---|---|
| Menthol | 0.6 g |
| Phenol | 1.2 mL |
| Camphor water | 60 mL |
| Lime water | Quantity sufficient to make 120 mL of formulation |

FIG. 3

| **Table 4** | |
|---|---|
| Menthol | 0.2 mg - 1.0mg |
| Lidocaine | 0.25% - 5% |
| Phenol | 0.6 mL - 2.0 mL |
| Camphor water | 60 mL |
| Lime water | Quantity sufficient to make 120 mL of formulation |

FIG. 4

FORMULATION AND METHOD OF USE OF A TREATMENT FOR SHINGLES PAIN

CROSS REFERENCE TO RELATED APPLICATIONS

This disclosure claims the benefit of U.S. Provisional Application No. 61/846,690 filed on Jul. 16, 2013 which is hereby incorporated by reference.

FIELD OF THE DISCLOSURE

The present disclosure relates generally to a pharmaceutical formulation to treat pain associated with shingles. In particular, the present disclosure is related to a unique composition for a lotion to treat pain associated with shingles.

BACKGROUND

Shingles, also known as zoster or herpes zoster, is caused by the varicella zoster virus. Almost one out of every three people in the United States will develop shingles in their lifetime, and there are an estimated one million cases of shingles each year in the United States. Anyone who has recovered from chickenpox may develop shingles. Although children can develop shingles, the risk of developing shingles increases with age. About half of all cases occur in adults 60 years and older.

After a person recovers from chickenpox, the varicella zoster virus remains dormant in the body. For reasons that are not fully known, the virus can reactivate years later, causing shingles.

Shingles is a painful rash that develops on one side of the face or body. The rash forms blisters that typically scab over in 7-10 days and clears up within 2-4 weeks. Before the rash develops, shingles sufferers often have pain, itching or tingling in the area where the rash will develop. This may happen anywhere from 1 to 5 days before the rash appears.

Several antiviral medications help shorten the length and severity of the illness, but there is currently no known cure. Analgesics may help relieve the pain caused by shingles, but there is no pharmaceutical agent that will address all symptoms of shingles.

SUMMARY

A pharmaceutical formulation for treatment of shingles is provided. The formulation includes between 0.2 mg of menthol per 120 mL of the formulation and 1.0 mg of menthol per 120 mL of the formulation, camphor water, lime water, and a local anesthetic. The local anesthetic includes one of between 0.6 mL of phenol per 120 mL of the formulation and 2.0 mL of phenol per 120 mL of the formulation and between 0.25% concentration by weight of lidocaine and 5% concentration by weight of lidocaine.

BRIEF DESCRIPTION OF THE DRAWINGS

Non-limiting and non-exhaustive embodiments of the present disclosure are described with reference to the following figures, wherein like reference numerals refer to like parts throughout the various views unless otherwise specified.

FIG. 1 is a table illustrating ranges of included ingredients in an exemplary embodiment of the disclosed formulation utilizing phenol, in accordance with the present disclosure;

FIG. 2 is a table illustrating ranges of included ingredients in an exemplary embodiment of the disclosed formulation utilizing lidocaine, in accordance with the present disclosure;

FIG. 3 is a table illustrating an exemplary embodiment of the disclosed formulation, in accordance with the present disclosure;

FIG. 4 is a table illustrating ranges of included ingredients in an exemplary embodiment of the disclosed formulation utilizing both phenol and lidocaine, in accordance with the present disclosure.

DETAILED DESCRIPTION

Figure 5:
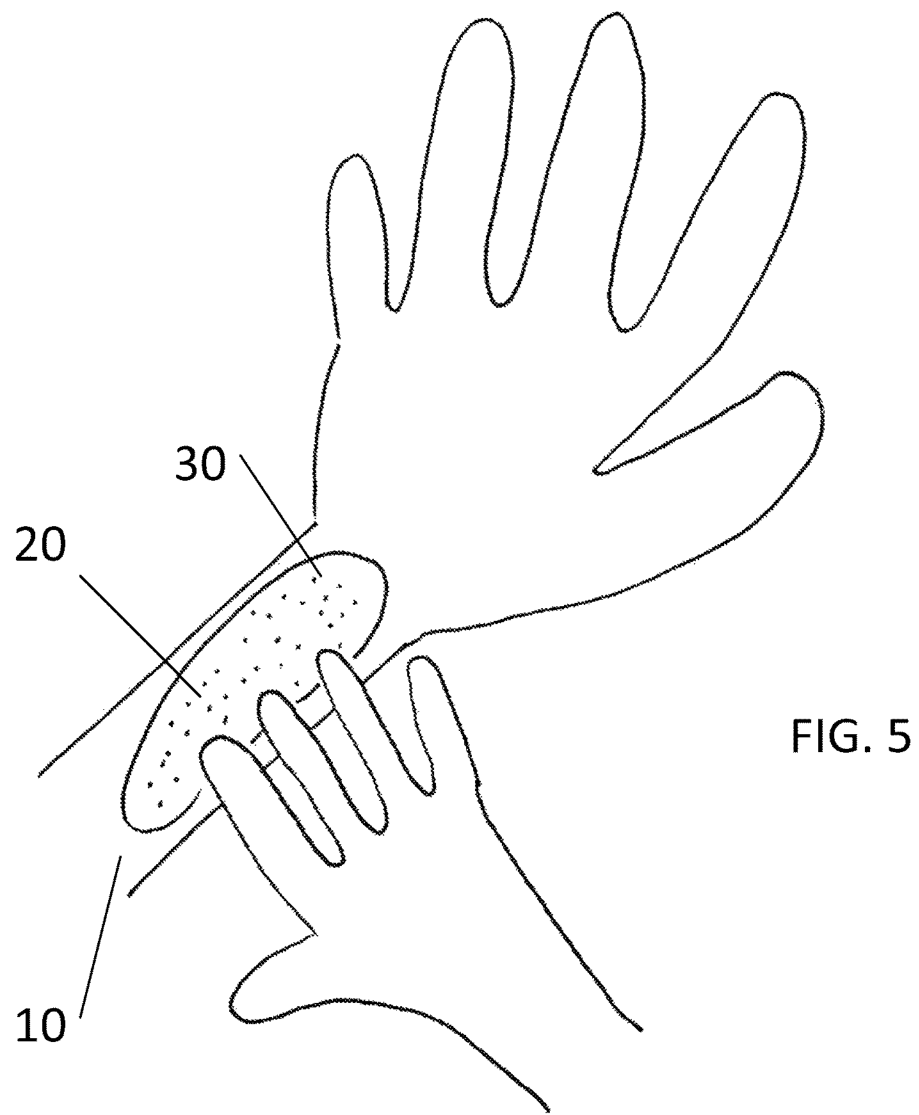
FIG. 5 illustrates the formulation being applied to an exemplary patch of affected skin, in accordance with the present disclosure.

In the following description, numerous specific details are set forth in order to provide a thorough understanding of the present disclosure. It will be apparent, however, to one having ordinary skill in the art that the specific detail need not be employed to practice the present disclosure. In other instances, well-known materials or methods have not been described in detail in order to avoid obscuring the present disclosure.

Reference throughout this specification to "one embodiment", "an embodiment", "one example" or "an example" means that a particular feature, structure or characteristic described in connection with the embodiment or example is included in at least one embodiment of the present disclosure. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

There are an estimated one million cases of shingles in the United States per year. Shingles sufferers require an effective way to relieve pain associated with shingles. The disclosure described herein is a pharmaceutical formulation which temporarily relieves pain associated with shingles. The disclosure is not intended to cure or treat the underlying disease.

An analgesic is any member of the group of drugs used to achieve relief from pain without eliminating sensation. Analgesic drugs act in various ways on the human nervous system. Health care providers choose analgesics based on type of pain and route of administration, among other considerations.

Analgesics are distinct from anesthetics. An anesthetic is any member of the group of drugs used to achieve temporary, reversible loss of sensation in the human body. Local anesthetics cause a temporary, reversible loss of sensation in a limited region of the body and do not cause loss of consciousness.

Both anesthetics and analgesics may be applied topically to human skin to cause temporary loss of sensation and temporarily pain relief, respectively.

An effective treatment for pain associated with shingles could be a topical formulation containing both an analgesic to temporarily relieve pain and an anesthetic to numb affected areas. In one embodiment, such a topical formulation could be a lotion. A lotion is a liquid or semi-liquid preparation that contains one or more active ingredients in an appropriate vehicle. Lotions are intended to be applied to unbroken skin. Other preparations, such as gels and creams, which have higher viscosity than lotions, are envisioned.

A pharmaceutical formulation to relieve pain associated with shingles or a method to produce such a pharmaceutical formulation can be disclosed including menthol, phenol, camphor water and lime water. A pharmaceutical formulation to relieve pain associated with shingles or a method to produce such a pharmaceutical formulation can be disclosed utilizing menthol as an ingredient with a minimum of 0.2 mg per preparation and a maximum of 1.0 mg per preparation. A pharmaceutical formulation to relieve pain associated with shingles or a method to produce such a pharmaceutical formulation can be disclosed utilizing phenol as an ingredient with a minimum of 0.6 mL per preparation and a maximum of 2.0 mL per preparation. A pharmaceutical formulation to relieve pain associated with shingles or a method to produce such a pharmaceutical formulation can be disclosed utilizing lidocaine as an ingredient, for example, replacing the phenol in the formulation, with a minimum of 0.25% concentration by weight and a maximum of 5% concentration by weight lidocaine per preparation.

In some embodiments, lidocaine can be substituted for phenol. Lidocaine is well known in the art as a local anesthetic. It is used topically to relieve itching, burning and pain from inflammation of the skin. In another embodiment, lidocaine can be used in addition to phenol. A exemplary formulation can include phenol as an ingredient with a minimum of 0.6 mL per preparation and a maximum of 2.0 mL per 120 mL preparation and lidocaine as an additional ingredient, with a minimum of 0.25% concentration by weight and a maximum of 5% concentration by weight lidocaine per 120 mL preparation.

FIG. 1 illustrates Table 1, which illustrates ranges of included ingredients in an exemplary embodiment of the disclosed formulation utilizing phenol.

FIG. 2 illustrates Table 2, which illustrates ranges of included ingredients in an exemplary embodiment of the disclosed formulation utilizing lidocaine.

FIG. 3 illustrates Table 3, which illustrates an exemplary embodiment that a lotion to relieve shingles pain can take, with an exemplary composition including 0.6 g menthol, 1.2 mL phenol, 60 mL camphor water and a quantity of lime water sufficient to produce 120 mL of lotion. Other compositions are envisioned.

FIG. 4 is a table illustrating ranges of included ingredients in an exemplary embodiment of the disclosed formulation utilizing both phenol and lidocaine.

Menthol is an ingredient that is well known in the art and has been used in pharmaceutical formulations for many years. It has analgesic and counter-irritant properties, and can function as a local anesthetic. When applied topically, menthol provides a cooling sensation to the skin.

Phenol is also well known in the art and has been used in pharmaceutical formulations for many years. It is an effective topical anesthetic and analgesic that cools and numbs skin on contact. In addition, it has antipruritic, or itch-relieving, properties, and may improve a preparation's effectiveness in itch relief.

Camphor water and lime water (also known as a saturated solution of calcium hydroxide) are well known in the art. Both camphor water and lime water are used herein as drying agents, but may serve other purposes in the disclosed disclosure.

In one embodiment, the disclosed disclosure is prepared by a pharmacist as follows.

Camphor water is prepared by shaving down a 1-2 g block of camphor. The camphor is then placed in a siphon. Boiling filtered water is then poured through the siphon, up to 1 pint. The shaved camphor is then placed in the bottle with the filtered water, and the bottle is shaken well.

Lime water is prepared by adding 28 g of calcium hydroxide to 1 gallon of distilled water. The mixture should be shaken periodically for up to 8 hours and then should be allowed to settle. Lime water should be poured off only from the top of this settled mixture.

Menthol in the amount of 0.6 g is crushed in a mortar and pestle. Phenol in the amount of 1.2 mL is added and mixed together with the crushed menthol. Camphor water in the amount of 60 mL is added to the mixture of menthol and phenol. Finally, a quantity of lime water sufficient to bring the mixture to 120 mL is added to the mixture of menthol, phenol and camphor water.

Other methods of preparation of the disclosed disclosure are envisioned, for example, manufacture in larger-scale proportions in a pharmacy or in a commercial setting.

The disclosure disclosed herein can be applied topically to affected areas of the skin every 3-4 hours as needed to relieve pain associated with shingles. It is envisioned that the disclosure disclosed herein could be used to treat other skin conditions.

In some embodiments, the pharmaceutical formulation could be sprayed upon the skin, for example, by a bottle utilizing a spray/atomizer pump device. In other embodiments, a patch or other means of covering affected skin could be impregnated with the pharmaceutical formulation, and such an impregnated patch applied or adhered to the skin of a person suffering from shingles.

FIG. 5 illustrates the formulation being applied to an exemplary patch of affected skin. Arm 10 is illustrated including affected skin 20. Exemplary lotion 30 is illustrated being spread over and applied to the affected skin 20. It will be appreciated that a spray-on liquid or a viscous gel can similarly be applied as is lotion 30.

The above description of illustrated examples of the present disclosure, including what is described in the Abstract, are not intended to be exhaustive or to be limitation to the precise forms disclosed. While specific embodiments of, and examples for, the disclosure are described herein for illustrative purposes, various equivalent modifications are possible without departing from the broader spirit and scope of the present disclosure. Indeed, it is appreciated that the specific example voltages, currents, frequencies, power range values, times, etc., are provided for explanation purposes and that other values may also be employed in other embodiments and examples in accordance with the teachings of the present disclosure.

What is claimed is:

1. A topical pharmaceutical formulation for the treatment of shingles, the formulation comprising:

menthol, in an amount of between 0.2 mg-1.0 mg per 120 mL of the formulation;

camphor water;

lime water, in a sufficient concentration to dry the skin of a patient; and a local anesthetic selected from the group consisting of phenol and lidocaine;

wherein the phenol, if present, is in an amount of between 0.6-2.0 mL per 120 mL of the formulation;

wherein the lidocaine, if present, is in a concentration of between 0.25% to 5% by weight of the formulation; and wherein the lime water is prepared by adding 28 grams of calcium hydroxide to one gallon of distilled water.

2. The formulation of claim 1, wherein the menthol is provided at 0.6 mg per 120 mL of the formulation.

3. The formulation of claim 2, wherein the local anesthetic comprises the phenol; and wherein the phenol is provided at 1.2 mL per 120 mL of the formulation.

4. The formulation of claim 1, wherein the local anesthetic comprises the phenol; and wherein the phenol is provided at 1.2 mL per 120 mL of the formulation.

5. The formulation of claim 4, further comprising between 0.25% concentration by weight of lidocaine and 5% concentration by weight of lidocaine.

6. The formulation of claim 1, wherein the camphor water is provided at 60 mL per 120 mL of the formulation.

7. The formulation of claim 1, wherein the formulation is provided as a lotion.

8. The formulation of claim 1, wherein the formulation is provided as a gel.

9. The formulation of claim 1, wherein the formulation is provided as a spray-on liquid.

10. A topical pharmaceutical formulation for the treatment of shingles, the formulation comprising:

menthol, in an amount of between 0.2 mg-1.0 mg per 120 mL of the formulation;

camphor water;

lime water, in a sufficient concentration to dry the skin of a patient; and a local anesthetic selected from the group consisting of phenol, lidocaine, and mixtures thereof;

wherein the phenol, if present, is in an amount of between 0.6-2.0 mL per 120 mL of the formulation;

wherein the lidocaine, if present, is in a concentration of between 0.25% to 5% by weight of the formulation;

wherein the lime water is prepared by adding 28 grams of calcium hydroxide to one gallon of distilled water; and wherein the pharmaceutical formulation is in the form of a lotion.

11. The formulation of claim 10, wherein the menthol is provided at 0.6 mg per 120 mL of the formulation.

12. The formulation of claim 11, wherein the phenol is provided at 1.2 mL per 120 mL of the formulation.

13. The formulation of claim 10, wherein the phenol is provided at 1.2 mL per 120 mL of the formulation.

14. The formulation of claim 10, wherein the camphor water is provided at 60 mL per 120 mL of the formulation.

15. The formulation of claim 10, wherein the lotion further comprises between 0.25% concentration by weight of lidocaine and 5% concentration by weight of lidocaine.

* * * * *